United States Patent [19]

Markezich

[11] 4,335,039
[45] Jun. 15, 1982

[54] THERMALLY STABLE POLYCARBONATE COMPOSITIONS

[75] Inventor: Ronald L. Markezich, Mt. Vernon, Ind.

[73] Assignee: General Electric Company, Mt. Vernon, Ind.

[21] Appl. No.: 957,427

[22] Filed: Nov. 2, 1978

[51] Int. Cl.³ .......................... C08K 5/15; C08K 5/52
[52] U.S. Cl. .................................... 524/108; 524/611
[58] Field of Search ...................... 260/340.7, 45.8 A

[56] References Cited

U.S. PATENT DOCUMENTS

| | | | |
|---|---|---|---|
| 3,096,345 | 7/1963 | Hechenbleikner et al. | 260/340.7 |
| 3,209,013 | 9/1965 | Hechenbleikner et al. | 260/333 |
| 3,231,531 | 1/1966 | Buckley et al. | 260/23 X A |
| 3,305,520 | 2/1967 | Fritz et al. | 260/45.7 PH |
| 3,489,716 | 1/1970 | Calkins | 260/37 PC |
| 3,794,629 | 2/1974 | Eimers et al. | 260/45.8 A |
| 4,073,769 | 2/1978 | Eimers et al. | 260/45.8 A |
| 4,102,859 | 7/1978 | Eimers et al. | 260/45.8 A |

OTHER PUBLICATIONS

Furukawa et al., "Polymerization of Aldehydes and Oxides", 1963, pp. 13–22.

Primary Examiner—Maurice J. Welsh
Assistant Examiner—R. A. White
Attorney, Agent, or Firm—Martin B. Barancik; William F. Mufatti

[57] ABSTRACT

Thermally stable polycarbonate compositions are obtained by admixing with a high molecular weight aromatic polycarbonate resin a stabilizing amount of a dioxane phosphite.

7 Claims, No Drawings

THERMALLY STABLE POLYCARBONATE COMPOSITIONS

This invention relates to thermally stable polycarbonate compositions comprising an admixture of an aromatic polycarbonate and a stabilizing amount of a dioxane phosphite.

BACKGROUND OF THE INVENTION

In the past, much effort has been expended in preparing thermally stable polycarbonate compositions which would be color stable at elevated temperatures and particularly at the high molding temperatures generally employed to prepare molded polycarbonate articles. Many different additives have been found that are quite suitable for rendering polycarbonates heat and color stable. Particularly useful are triorgano phosphites such as are disclosed in U.S. Pat. No. 3,305,520. In addition, U.S. Pat. Nos. 3,729,440 and 3,953,388 disclose thermally stable aromatic polycarbonates containing a phosphinite and an epoxy compound. Further, U.S. Pat. No. 3,794,629 discloses chemically stable aromatic polycarbonates containing oxetane phosphites and U.S. Pat. No. 3,978,020 discloses thermally stable aromatic polycarbonates containing phosphonites which include epoxy compounds.

Polycarbonates are also used for producing bottles; however, these bottles become hazy after sterilization in water or exposure to moisture at elevated temperatures. U.S. Pat. No. 3,839,247 discloses a water clear polycarbonate composition which can be used to mold bottles wherein the polycarbonate composition contains an aromatic epoxy or an aliphatic epoxy compound as a stabilizer.

Copending application Ser. No. 957,426, filed Nov. 2, 1978, now issued as U.S. Pat. No. 4,247,448, discloses the use of phosphonite oxetanes with aromatic polycarbonates, copending application Ser. No. 957,429, filed Nov. 2, 1978, now abandoned, discloses the use of hindered phenol phosphite oxetanes, copending application Ser. No. 957,428, filed Nov. 2, 1978, discloses the use of hindered phenol phosphonite oxetanes, and copending application Ser. No. 957,430, filed Nov. 2, 1978, discloses the use of hindered phenol phosphites all with aromatic polycarbonate, all of these copending applications being assigned to the same assignee as this case.

DESCRIPTION OF THE INVENTION

It has been discovered that when an aromatic polycarbonate is admixed with a dioxane phosphite, the resulting polycarbonate composition has improved thermal stability as exemplified by its resistance to yellowing when subjected to high molding temperatures.

The dioxane phosphites that can be used in the present invention are represented by the general structure:

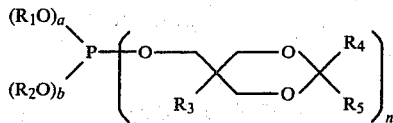

wherein n is 1–3; a plus b equal 3−n; $R_1$ and $R_2$ can be the same or different and can each independently be an alkyl of $C_1$ to $C_{30}$ or an aryl of $C_6$ up to about $C_{30}$; preferably $C_6$–$C_{12}$; and, $R_3$, $R_4$ and $R_5$ can each be the same or different and can each independently be hydrogen alkyl, aryl, aralkyl, halomethyl, cyanomethyl, alkoxymethyl, aryloxymethyl, aralkyloxymethyl or acyloxymethyl.

Thus, $R_1$ and $R_2$ in formula I can independently be unsubstituted and halogen substituted alkyl, aryl, cycloalkyl, aralkyl and alkaryl radicals of about $C_1$–$C_{30}$ so that typical phosphites that can be employed in the present invention are those wherein $R_1$ and $R_2$ can be alkyl such as methyl, ethyl, n-propyl, isopropyl, n-butyl, sec-butyl, tertiary butyl, n-amyl, isoamyl, tertiary amyl, n-hexyl, dodecyl, nonyl, and the like; cycloalkyl such as cyclohexyl, 4-ethylcyclohexyl, 4-isopropylcyclohexyl, and the like; aryl such as phenyl, naphthyl, 2-naphthyl, biphenyl of terphenyl, and the like; aralkyl such as benzyl, phenylethyl, 2-phenylethyl, 1-phenylpropyl, 2-phenylpropyl, and the like; alkaryl such as p-tolyl, m-tolyl, 2,6-xylyl, o-tolyl, p-cumyl, m-cumyl, o-cumyl, mesityl, p-tertiary butylphenyl, and the like; and, haloaryl such as 2-chlorophenyl, 2,4,6-trichlorophenyl, 2,4,6-tribromophenyl, and the like, wherein the substituted portions thereof can be halogen atoms.

The phosphites of the invention can be prepared by methods known to those skilled in the art such as are described in *Organic Phosphorous Compounds*, Vol. 5, edited by G. M. Kosolapoff and L. Maier (1972) pages 39–41, which is incorporated herein by reference thereto.

The dioxane phosphite is admixed with the aromatic polycarbonate in a stabilizing amount which is generally on the order of about 0.005–1.0, preferably 0.01–0.50 and optimumly about 0.02–0.20 weight percent, based upon the weight of the aromatic polycarbonate.

The aromatic polycarbonate that can be employed in the practice of this invention are homopolymers and copolymers and mixtures thereof that are prepared by reacting a dihydric phenol with a carbonate precursor.

The dihydric phenols that can be employed are bisphenols such as bis(4-hydroxyphenyl)methane, 2,2-bis(4-hydroxyphenyl)propane(bisphenol-A), 2,2-bis(4-,hydroxy-3-methylphenyl)propane, 4,4-bis(4-hydroxyphenyl)heptane, 2,2-bis(4-hydroxy-3,5-dichlorophenyl)-propane, 2,2-bis(4-hydroxy-3,5-dibromophenyl)propane, etc.; dihydric phenol ethers such as bis(4-hydroxyphenyl)ether, bis(3,5-dichloro-4-hydroxyphenyl)ether, etc.; dihydroxydiphenyls such as p,p'-dihydroxydiphenyl, 3,3'-dichloro-4,4-dihydroxydiphenyl, etc.; dihydroxyaryl sulfones such as bis(4-hydroxyphenyl)sulfone, bis(3,5-dimethyl-4-hydroxyphenyl)sulfone, etc.; dihydroxy benzenes, resorcinol, hydroquinone, halo- and alkyl-substituted dihydroxy benzenes such as 1,4-dihydroxy-2,5-dichlorobenzene, 1,4-dihydroxy-3-methylbenzene, etc.; and dihydroxy diphenyl sulfoxides such as bis(4-hydroxyphenyl)sulfoixde, bis(3,5-dibromo-4-hydroxyphenyl)sulfoxide, etc. A variety of additional dihydric phenols are also available to provide carbonate polymers such as are disclosed in U.S. Pat. Nos. 2,999,835, 3,028,365 and 3,153,008. Also suitable for preparing the aromatic carbonate polymers are copolymers prepared from the above dihydric phenols copolymerized with halogen-containing dihydric phenols such as 2,2-bis(3,5-dichloro-4-hydroxyphenyl)propane, 2,2-bis(3,5-dibromo-4-hydroxyphenyl)propane, etc. It is also possible to employ two or more different dihydric phenols or a copolymer of a dihydric phenol with a glycol or with hydroxy or acid terminated polyester, or with a dibasic acid in the event a carbonate copolymer or interpolymer rather than a homopolymer is desired for use in the preparation of the aromatic polycarbonates of this invention as well as blends of any of the above materials.

The carbonate precursor can be either a carbonyl halide, a carbonate ester or a haloformate. The carbonyl halides which can be employed are carbonyl bromide, carbonyl chloride and mixtures thereof. Typical of the carbonate esters that can be employed are diphenyl carbonate, di-(halophenyl) carbonates such as di-(chlorophenyl) carbonate, di-(bromophenyl) carbonate, di-(trichlorophenyl) carbonate, di-(tribromophenyl) carbonate, etc.; di-(alkylphenyl) carbonate such as di-(tolyl) carbonate, etc., di-(naphthyl) carbonate, di-(chloronaphthyl) carbonate, phenyl tolyl carbonate, chlorophenyl chloronaphthyl carbonate, etc., or mixtures thereof. The haloformates suitable for use herein include bishaloformates of dihydric phenols (bischloroformates of hydroquinone, etc.) or glycols (bishaloformates of ethylene glycol, neopentyl glycol, polyethylene glycol, etc.). While other carbonate precursors will occur to those skilled in the art, carbonyl chloride, also known as phosgene, is preferred.

Also included are the polymeric derivatives of a dihydric phenol, a dicarboxylic acid and carbonic acid. These are disclosed in U.S. Pat. No. 3,169,121 which is incorporated herein by reference.

The aromatic polycarbonates of this invention are prepared by employing a molecular weight regulator, an acid acceptor and a catalyst. The molecular weight regulators which can be employed include monohydric phenols such as phenol, chroman-I, paratertiary-butylphenol, parabromophenol, primary and secondary amines, etc. Preferably, phenol is employed as the molecular weight regulator.

A suitable acid acceptor can be either an organic or an inorganic acid acceptor. A suitable organic acid acceptor is a tertiary amine and includes such materials as pyridine, triethylamine, dimethylaniline, tributylamine, etc. The inorganic acid acceptor can be one which can be either a hydroxide, a carbonate, a bicarbonate, or a phosphate of an alkali or alkaline earth metal.

The catalysts which can be employed can be any of the suitable catalysts that aid the polymerization of bisphenol-A with phosgene. Suitable catalysts include tertiary amines such as triethylamine, tripropylamine, N,N-dimethylaniline, quaternary ammonium compounds such as tetraethylammonium bromide, cetyl triethylammonium bromide, tetra-n-heptylammonium iodide, tetra-n-propylammonium bromide, tetramethylammonium chloride, tetramethylammonium hydroxide, tetra-n-butylammonium iodide, benzyl trimethylammonium chloride and quaternary phosphonium compounds such as n-butyltriphenyl phosphonium bromide and methyltriphenyl phosphonium bromide.

Also included herein are branched polycarbonates wherein a polyfunctional aromatic compound is reacted with the dihydric phenol and carbonate precursor to provide a thermoplastic randomly branched polycarbonate.

These polyfunctional aromatic compounds contain at least three functional groups which are carboxyl, carboxylic anhydride, haloformyl or mixtures thereof. Examples of these polyfunctional aromatic compounds include trimellitic anhydride, trimellitic acid, trimellityl trichloride, 4-chloroformyl phthalic anhydride, pyromellitic acid, pyromellitic dianhydride, mellitic acid, mellitic anhydride, trimesic acid, benzophenonetetracarboxylic acid, benzophenonetetracarboxylic anhydride, and the like. The preferred polyfunctional aromatic compounds are trimellitic anhydride or trimellitic acid, or their haloformyl derivatives.

Also included herein are blends of a linear polycarbonate and a branched polycarbonate.

DESCRIPTION OF THE PREFERRED EMBODIMENT

The following examples are set forth to more clearly illustrate the invention. Unless otherwise specified, parts or percents are by weight.

EXAMPLE 1

Method of Preparing a New Dioxane Phosphite:

[(5-Ethyl-1,3-dioxanyl-5)-methyl]diphenyl phosphite

One (1) mole of triphenyl phosphite was reacted with 1 mole of 5-ethyl-5-hydroxymethyl-1,3-dioxane in the presence of a basic catalyst and 1 mole of phenol was distilled off. Upon further distillation at 162°–171° C. under a vacuum of 0.15 mm. Hg., the product, [(5-ethyl-1,3-dioxanyl-5)-methyl]diphenyl phosphite was recovered as a clear, colorless liquid. The proton nuclear magnetic resonance (NMR) analysis revealed 5 aliphatic protons from 0.6 to 1.4δ, 8 protons adjacent to the oxygens from 3.3 to 5.0δ, and 10 aromatic protons from 6.8 to 7.4δ.

Structure:

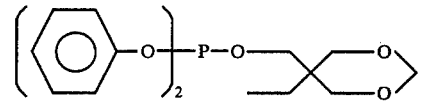

EXAMPLE 2

Method of Preparing a New Dioxane Phosphite:

Bis[(5-ethyl-1,3-dioxanyl-5)-methyl]phenyl phosphite

One (1) mole of triphenyl phosphite was reacted with 2 moles of 5-ethyl-5-hydroxymethyl-1,3-dioxane in the presence of a basic catalyst and 2 moles of phenol were distilled off. Upon further distillation at 180° C. under a vacuum of 0.2 mm. Hg., the product, bis[(5-ethyl-1,3-dioxanyl-5)-methyl]phenyl phosphite was recovered as a clear colorless liquid. Proton NMR analysis revealed 10.8 aliphatic protons from 0.6 to 1.6δ, 14.4 protons adjacent to the oxygens from 3.3 to 5.0δ, and 5.8 aromatic protons from 7.0 to 7.4δ.

Structure:

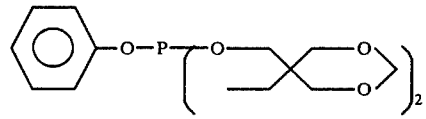

EXAMPLE 3

Method of Preparing a New Dioxane Phosphite:

Tris[(5-ethyl-1,3-dioxanyl-5)-methyl]phosphite

One (1) mole of triphenyl phosphite was reacted with 3 moles of 5-ethyl-5-hydroxymethyl-1,3-dioxane in the presence of a basic catalyst and 3 moles of phenol were distilled off. Upon further distillation at 218° C. under a vacuum of 0.4 mm. Hg., the product, tris[(5-ethyl-1,3-dioxanyl-5)-methyl]phosphite was recovered as a clear, colorless liquid. Proton NMR analysis revealed 15.8 aliphatic protons from 0.6 to 1.6δ, and 23.2 protons adjacent to the oxygens from 3.3 to 5.0δ.

Structure:

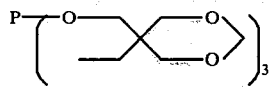

EXAMPLE 4

A polycarbonate composition of a homopolymer of 2,2-bis(4-hydroxyphenyl)propane (bisphenol-A) was prepared by reacting essentially equimolar amounts of bisphenol-A and phosgene in an organic medium with triethylamine, sodium hydroxide and phenol under standard conditions and was mixed with the stabilizers shown in Table 1 by tumbling the ingredients in a laboratory tumbler. This mixture was then fed to an extruder, which extruder was operated at about 500° F., and the extruded strands chopped into pellets. The pellets were then injected molded at 600° F. and 680° F. into test samples of about 3 inches by 2 inches by ⅛ inch thick. Thermal stability to discoloration of the test samples was measured in accordance with ASTM Yellowness Index (YI) Test D1925 on samples molded at 600° F. and 680° F. The results obtained are set forth in Table I below.

TABLE I

| Stabilizer | Amount (wt %) | Thermal Stability YI of Test Samples Molded At: | |
|---|---|---|---|
| | | 600° F. | 680° F. |
| *A | 0.1 | 2.5 | 8.8 |
| Example 1 | 0.03 | 2.5 | 5.8 |
| Example 1 | 0.05 | 2.4 | 5.4 |
| Example 1 | 0.1 | 2.5 | 5.8 |

*As disclosed in Ger. Pat. 1,694,285 and referred to in U.S. Pat. No. 3,794,629: 1 part octyldiphenyl phosphite 2 parts 3,4-epoxy-cyclohexylemethyl-3,4-epoxycyclohexane carboxylate The results in Table I above reveal that the stabilizer of Example 1 is about the same as prior art stabilizer A when incorporated at the same or lower concentrations into test samples molded at 600° F. But when incorporated into test samples molded at 680° F., the stabilizers of Example 1 impart significantly better stability than prior art stabilizer A, even at greatly reduced levels.

EXAMPLE 5

The procedure of Example 4 was followed to prepare additional test samples which also were subjected to the YI stability test described in Example 4. The results obtained are set forth in Table II below wherein "control" identifies the polycarbonate composition prepared as in Example 4 without stabilizer.

TABLE II

| Stabilizer | Amount (wt %) | YI of Test Samples Molded At: | |
|---|---|---|---|
| | | 600° F. | 680° F. |
| Control | — | 3.5 | 6.3 |
| A | 0.1 | 2.1 | 6.9 |
| Example 2 | 0.04 | 2.0 | 5.0 |
| Example 2 | 0.09 | 2.0 | 4.5 |
| Example 3 | 0.05 | 1.6 | 4.2 |
| Example 3 | 0.1 | 1.5 | 5.0 |
| Example 3 / **B | 0.05 / 0.03 | 1.7 | 5.5 |

**3,4-epoxy-cyclohexylmethyl-3,4-epoxycyclohexane carboxylate.

It can be seen from the results in Table II that the stabilizers of Examples 2 and 3 performed significantly better than prior art stabilizer A at both the 600° F. and 680° F. molding temperatures, even at substantially reduced concentrations.

Although the stabilizers of the invention have been particularly shown employed with high molecular weight aromatic polycarbonates, it should be understood that this has been by way of illustrating the general efficacy of these stabilizers with thermoplastic resins. As will be apparent to the skilled artisan, the stabilizers of the invention can also be employed with other thermoplastics such as polyolefins, polyvinyl chloride, polyesters and the like, with substantially similar facility and efficacy.

What is claimed is:

1. A thermally stabilized aromatic polycarbonate composition comprising an admixture of a high molecular weight aromatic polycarbonate and a stabilizing amount of a dioxane phosphite stabilizer represented by the general structure:

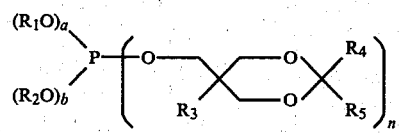

wherein n is 1 to 3; a plus b equal 3-n; $R_1$ and $R_2$ can be the same or different and can each independently be an alkyl of $C_1$ to $C_{30}$ or an aryl of $C_6$ to about $C_{30}$; and, $R_3$, $R_4$ and $R_5$ can be the same or different and can each independently be hydrogen, alkyl, aryl, aralkyl, halomethyl, cyanomethyl, alkoxymethyl, aryloxymethyl, aralkyloxymethyl or acyloxymethyl.

2. The composition of claim 1 wherein the aryl of $R_1$ and $R_2$ is one having about $C_6$-$C_{12}$.

3. The composition of claim 1 wherein said dioxane phosphite stabilizer is a member selected from the group having the following structures:

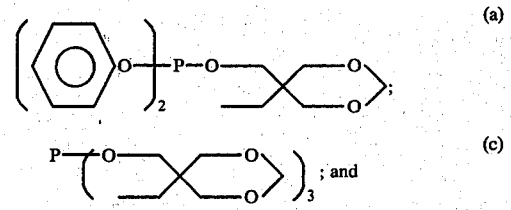

mixtures thereof.

4. The composition of claim 1 wherein said stabilizer is present in an amount of about 0.005-1.0 percent by weight of said aromatic polycarbonate.

5. The composition of claim 4 wherein said stabilizer is present in an amount of about 0.01-0.5 weight percent.

6. The composition of claim 1 wherein said aromatic polycarbonate is derived from 2,2-bis(4-hydroxyphenyl)propane.

7. The composition of claim 1 which includes a stabilizing amount of an epoxide co-stabilizer.

* * * * *

UNITED STATES PATENT AND TRADEMARK OFFICE
CERTIFICATE OF CORRECTION

PATENT NO. : 4,335,039
DATED : 6/15/82
INVENTOR(S) : Ronald L. Markezich

It is certified that error appears in the above-identified patent and that said Letters Patent are hereby corrected as shown below:

Column 6, line 52 - structure (b) has been omitted.

Structure (b) is as follows:

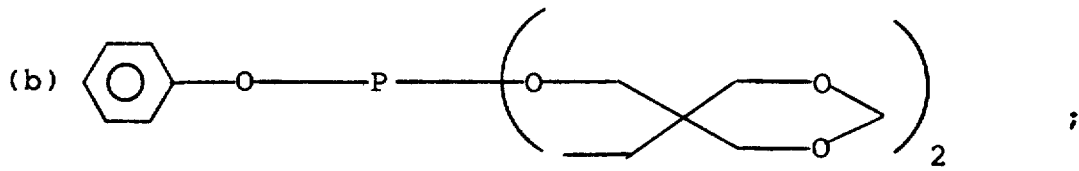

Signed and Sealed this

Sixth Day of March 1984

[SEAL]

Attest:

Attesting Officer

GERALD J. MOSSINGHOFF

Commissioner of Patents and Trademarks